United States Patent [19]

Walter et al.

[11] Patent Number: 4,859,591

[45] Date of Patent: Aug. 22, 1989

[54] TRANSAMINATION PROCESS FOR PRODUCING AMINO ACIDS

[75] Inventors: James F. Walter, Ashton; Martin B. Sherwin, Potomac, both of Md.

[73] Assignee: W. R. Grace & Co.-Conn., New York, N.Y.

[21] Appl. No.: 83,603

[22] Filed: Aug. 7, 1987

Related U.S. Application Data

[63] Continuation-in-part of Ser. No. 627,969, Jul. 5, 1984.

[51] Int. Cl.$^4$ .................... C12P 13/04; C12P 13/22; C12N 9/10
[52] U.S. Cl. .................... 435/106; 435/108; 435/193
[58] Field of Search .................... 435/106, 108, 193

[56] References Cited

U.S. PATENT DOCUMENTS

| | | |
|---|---|---|
| 3,183,170 | 5/1965 | Kitai et al. |
| 4,518,692 | 5/1985 | Rozzel ............................ 435/106 |
| 4,525,454 | 6/1985 | Rozzel ............................ 435/106 |

FOREIGN PATENT DOCUMENTS 0135846  4/1985  European Pat. Off. ............ 435/106

OTHER PUBLICATIONS

Krebs; "The Effect of Inorganic Salts on the Ketone Decomposition of Oxalacetic Acid"; Biochem., vol. 36, pp. 303–305, 1942.

Bessman; "Preparation and Assay of Oxalacetic Acid"; Arch. Biochem., vol. 26, pp. 418–421, 1950.

Steinberger; "Metal Ion–Catalyzed Decarboxylation: A Model for an Enzyme System"; J. Amer. Chem. Soc., vol. 73, pp. 429–435, 1951.

Oishi; "The Microbial Production of Amino Acids"; Micro. Prod. of Amino Acids; pp. 440–446, 1972.

Weast; "Table of Physical Constants of Inorganic Compounds"; Handbook of Chemistry and Physics, pp. B68, B103, and B106.

Dean; Lange's Handbook of Chemistry, Table 4–1, Physical Constants of Inorganic Compounds (12th Ed.).

*Primary Examiner*—H. M. S. Sneed
*Assistant Examiner*—J. Saba
*Attorney, Agent, or Firm*—Jill H. Krafte

[57] ABSTRACT

A process is disclosed for catalyzing the transamination of an amino acid precursor to the corresponding L-amino acid by using aspartic acid as the amino donor and by adding certain multivalent metal ions, in the form of solid metal particles or pieces, to the system to catalyze the decomposition of oxalacetic acid, a by-product of the transamination.

4 Claims, No Drawings

TRANSAMINATION PROCESS FOR PRODUCING AMINO ACIDS

This is a continuation-in-part of copending U.S. Ser. No. 627,969, "Improved Transamination Process for Producing Amino Acids" (Walter et al.), filed July 5, 1984.

BACKGROUND OF THE INVENTION

This invention relates generally to an improved process for the production of L-amino acids (hereinafter "amino acids") from their α-keto acid precursors by biological transamination using aspartic acid as the amino donor. More specifically, the process disclosed herein is designed to improve the rate and yield of the transamination by increasing the rate of decomposition of oxalacetic acid, one of the reaction by-products. This results in a significant increase in the reaction rate such that substantially all of the precursor is consumed in the transamination. By eliminating the equilibrium constraint on the transamination and by allowing more precursor to be converted, amino acid yields of over 90 percent can be achieved. The reaction is catalyzed in this manner by the addition of metal ions, as solid metal particles or pieces comprising aluminum oxide, ferric oxide, lead oxide or zinc oxide, to the transamination reaction system.

It is known that amino acid precursors may be converted enzymatically to their corresponding L-amino acids. For example, U.S. Pat. No. 3,183,170 (Kitai et al.) discloses the transamination of phenylpyruvic acid in the presence of a multi enzyme system obtained from various sources, including bacterial cells, dried cells, cell macerates or enzyme solutions. U.S. Ser. No. 520,632 (Fusee), filed Aug. 5, 1983, now abandoned, discloses the microbial transamination of α-keto acids to amino acids in fed-batch fermentations using conventional precursors to convert, for example, phenylpyruvic acid to L-phenylalanine, α-ketoisocaproic acid to L-leucine, α-ketoisovaleric acid to L-valine, etc.

The α-keto acid to amino acid biotransformation is an enzymatic transamination which results in the exchange of the amino group of the amino donor and the keto group of the precursor. It generally has been recognized that enzymatic transamination is an equilibrium reaction. For example, Oishi, in Ch. 16 of *The Microbial Production of Amino Acids*, (Yamada et al., Ed.), "Production from Precursor Keto Acids," pp. 440-46 (1972), notes that the use of aminotransferase has necessitated a high concentration of the amino donor for a high product yield. U.S. Pat. No. 3,183,170 (Kitai et al.) reports that in a transamination reaction using L-glutamic acid as the amino donor, the equilibrium is shifted favorably to the right by converting the alpha-keto glutaric acid resulting from the transamination back to L-glutamic acid by reductive amination as fast as the α-keto glutaric acid is formed.

In conventional transamination processes, a number of compounds have been used as the amino donor. Oishi, at pp. 435-52 of the Yamada et al. text, states that the best amino donors are L-aspartic acid, L-leucine, L-isoleucine and L-glutamic acid and that better results are obtained when these amino acids are used in combination than when they are used singly. U.S. Ser. No. 568,300 (Walter), filed on Jan. 5, 1984, now abandoned, discloses a process for driving a microbial transamination reaction towards completion by using a solution comprising approximately equimolar amounts of aspartic acid and phenylalanine precursor, pre-growing the microorganisms in the presence of the precursor, employing the biological catalyst in the form of dried cells, and/or increasing the biological catalyst loading of the system.

Oxalacetic acid (also known as oxaloacetic acid, oxosuccinic acid or keto succinic acid) is a by-product of enzymatic transamination when aspartic acid is used as the amino donor. Oxalacetic acid has been studied in other contexts and has been found to decompose by various mechanisms. Bessman, "Preparation and Assay of Oxalacetic Acid," Arch. Biochem., Vol. 26, pp. 418-21 (1950), reports spontaneous decomposition of oxalacetic acid, which is catalyzed by a number of substances, Krebs, "The Effect of Inorganic Salts on the Ketone Decomposition of Oxalacetic Acid," J. Biochem., Vol. 36, pp. 303-05 (1942), reports that various inorganic salts increase the rate of decomposition of oxalacetic acid into pyruvic acid and carbon dioxide.

SUMMARY OF THE INVENTION

It has been found that, under conditions as disclosed herein, the transamination of an amino acid precursor to its corresponding amino acid, where aspartic acid is selected as the primary amino donor and the precursor is an α-keto acid, can be significantly improved by catalyzing the decomposition of the oxalacetic acid by-product of the transamination. The decomposition is catalyzed by addition of certain multivalent metal ions to the reaction system in the form of solid metal particles comprising aluminum oxide, ferric oxide, lead oxide or zinc oxide. The L-amino acid may be accumulated and collected. By decomposing oxalacetic acid in this manner, the equilibrium of the system is shifted dramatically to the right, driving the reaction substantially to completion. The result of this metal ion catalysis is to boost transamination rates and amino acid yields.

One of the purposes of this invention is to improve a biological transamination reaction by dramatically increasing the reaction rate and the overall yield of amino acid based on both aspartic acid and precursor. It is, therefore, possible to decrease the proportional quantities of precursor needed to achieve the desired product yield.

By substantially increasing the rate of transamination, the time required for the system to convert a given quantity of precursor will be decreased. Moreover, the increased reaction rate substantially decreases loss of product yield due to decomposition of the precursor. In addition, this leads to decreased contamination with unreacted precursor, making the product purification and recovery less burdensome.

A further object of the invention is to catalyze the basic transamination reaction by adding solid metal particles, thereby eliminating any need for separating metal salts from the desired amino acid product. It is also an object to provide a catalyzed transamination reaction system in which the catalyst (solid metal particles) is retained in the system and does not require replenishment.

Another object is to provide a reaction in which the α-keto acid precursor does not need to be pure and which will overcome the inhibition effect of the impurities which may be present.

An overall object of the invention is to significantly reduce the costs associated with the production of amino acids by transamination.

DETAILED DESCRIPTION OF THE INVENTION

The invention disclosed herein provides a unique means for driving the transamination of an amino acid precursor to its corresponding L-amino acid, using aspartic acid as the amino donor and an appropriate -keto acid precursor, selecting a suitable intra- or extracellular transaminase, and coupling the transamination reaction with the catalyzed decomposition of the oxalacetic acid transamination by-product under conditions favorable for transaminase activity. The catalyzed decomposition is effected by the addition of multivalent metal ions in the form of solid metal particles or pieces comprising metal oxide to the reaction system and allowing the transamination to proceed significantly beyond equilibrium. The transamination may be accomplished by contacting a solution comprising the α-keto acid precursor and aspartic acid with the intra- or extracellular transaminase, that is, with a cell or enzyme preparation capable of mediating the transamination. The term "transaminase" as used herein refers to an enzyme or enzyme system capable of mediating the precursor-to-amino-acid conversion just described.

Microorganisms which already have been found useful in this type of transamination process are *Pseudomonas pseudoalcaligenes*, *Brevibacterium thiogenitalis*, *Pseudomonas aeriginosa*, *Bacillus subtillus* and *Escherichia coli*, each of which mediate the transamination of phenylalanine precursor to L-phenylalanine. In addition, the latter four species of bacteria have been demonstrated to have activity for the production of other amino acids (e.g., L-tyrosine, L-leucine, L-isoleucine and L-valine) by transamination with aspartic acid as the donor. The group of microorganisms which will be useful in this invention will, of course, be much broader. Organisms belonging to the genus Aerobacter, halophilic organisms, and yeasts such as those belonging to the genus Candida have been found to be suitable. It is expected that any microorganism which is known to demonstrate transaminase activity for the production of amino acids and which can use aspartic acid as the amino donor will be useful in this method. In addition, it is contemplated that mixed cultures of suitable strains may be used.

The growth conditions should be selected on the basis of the particular microorganism used and will be within the knowledge and skill if a person working in this area. It is preferred that the conditions favor the rapid growth of healthy cells. For example, if *Pseudomonas pseudoalcaligenes* is used, temperature preferably is maintained at about 35° to about 39° C. and pH at about 7.5. Agitation and/or aeration is used in order to provide an aerobic environment. Suitable energy and nutrient sources should be provided.

The microorganisms are grown to some predetermined cell density or growth phase. The precise growth period and cell density is not critical because density may be increased after growth, if desired, by conventional means such as centrifugation or filtration. A typical growth period of about 12 to about 48 hours usually will provide a workable number of cells. The cells then are harvested and may be treated to permeabilize the cell membrane. This treatment may be by drying, sonicating, incubating with toluene or nonionic surfactants, etc. It may also be desired to immobilize the cells on a suitable substrate. If viable microorganisms are used in the method of this invention, it is preferred that they be capable of excreting the amino acid product into the medium for convenient and economical recovery. In cell preparations as described above, sufficient quantities of transaminase will be present in association with the cells or cellular material to carry out the reaction.

At least about 2.0 to about 200.0 grams of cells (dry weight) are used per liter of substrate solution, preferably at least about 4.0 to about 80.0 grams per liter. Regardless of the form in which the cells actually are used in the process, the indication of cell catalyst weights used herein are on a dry basis. Lower catalyst levels will allow significant amounts of the precursor to decompose before undergoing transamination. The extent of the precursor decomposition problem in conventional transaminations will vary, depending on the α-keto acid precursor and on the reaction conditions. For example, decomposition will be accelerated somewhat by the presence of multivalent metal salts, as well as by acidic pH conditions, ultraviolet light or the presence of oxygen.

Alternatively, a cell-free system can be used. The transamination is enzymatic and may proceed in a solution comprising the appropriate enzymes or transaminases. Therefore, it will be possible to use an enzyme preparation, i.e., a crude extract or an isolated and purified enzyme, for the transamination reaction. In yet another embodiment, the enzyme may be immobilized on a suitable substrate.

The amino acid precursor is an α-keto carboxylic acid or its salt. The α-keto acid selected for use with this process will depend upon which amino acid is the desired transamination product. For example, phenylpyruvic acid is converted to L-phenylalanine, α-ketoisocaproic acid to L-leucine, α-ketoisovaleric acid to L-valine, pyruvic acid to L-alanine, β-hydroxy-α-ketobutyric acid to L-threonine, p-hydroxyphenylpyruvic acid to L-tyrosine, 20 indole pyruvic acid to L-tryptophan, α-keto-β-methyl valeric acid to L-isoleucine, α-ketohistidinal acid (β-imidazolylpyruvic acid) to L-histidine, etc. As can be seen, conventional amino acid precursors are used in the inventive process. The precursor may be purified, or may be in unpurified form such as a sodium, calcium, potassium or ammonium hydroxide hydrolysate or a sulfuric acid precipitate.

In the preferred embodiment of this invention, a substrate solution comprising molar ratios of aspartic acid and amino acid precursor of about 1:2 to about 2:1 in a biocompatible buffer is prepared. Any biocompatible solvent or buffer which does not interfere with the reaction process and which will maintain the reaction system in the preferred pH range of about 6.5 to about 10.0 may be utilized. For example, about 0.1 to 0.5 M phosphate buffer has been found to be suitable. Alternatively, the pH can be controlled by adding a pH controller to the system to add base as needed. There will be tendency for the pH to drop as the transamination proceeds.

The amino donor for the improved transamination of this invention must be aspartic acid or must substantially comprise aspartic acid. It has been found that the highest amino acid yield is achieved when aspartic acid is the only amino donor present in the reaction system. By using aspartic acid as the amno donor, oxalacetic acid is formed as a by-product of the transamination. The oxalacetic acid is decomposed, both spontaneously and catalytically, to yield carbon dioxide and pyruvic acid.

Of course, it will be permissible to have other amino donors present in the system and for these to be utilized by the transaminase. However, to the extent that the transamination reaction incorporates non-aspartic acid amino donors, this improved process will not operate, as there is no oxalacetic acid by-product to decompose.

The presence of the cofactor pyridoxal-5-phosphate (P-5-P) is required to facilitate the transamination. This cofactor complexes with the enzyme, is transiently converted to pyridoxamine phosphate (PMP) and is regenerated in the overall reaction. It may be desired to add small amounts of P-5-P to enhance the transamination. For example, adding P-5-P to concentrations of about 1.0 $\mu$M, may be desired, although small quantities of the cofactor will be present with cellular material added to the reaction system.

There are three potentially rate-limiting reactions in this improved transamination process: (1) bioconversion of the precursor to amino acid, (2) decomposition of the $\alpha$-keto acid precursor to valueless products and (3) decomposition of the oxalacetic acid by-product. The first reaction, the bioconversion, easily may be driven by increasing the loading of the transamination catalyst, the catalyst being contained in the cellular material. By driving the first reaction, the extent of precursor decomposition (the second reaction) is decreased. Therefore, the critical rate-limiting step then becomes the oxalacetic acid decomposition. It can be seen that increasing the availability of transamination catalyst will be most advantageous only if the oxalacetic acid decomposition rate simultaneously is increased.

The decomposition of oxalacetic acid is a first order reaction, that is, the rate of decomposition is proportional to the concentration of oxalacetic acid in the system. At high concentrations, there is faster decomposition, but the rate slows as the decomposition lowers the concentration. The spontaneous decomposition rate for a concentration of 0.1 moles per liter is about $6.7 \times 10^{-3}$ moles per liter per hour. Removal of oxalacetic acid from the reaction system by spontaneous decomposition will tend to drive the conversion of precursor to amino acids towards completion. However, in the initial stages of a biologically catalyzed transamination, oxalacetic acid may be produced at a rate of up to 5 to 10 times faster than its spontaneous decomposition rate, or even faster, if the transamination system allows it. Thus, even with spontaneous decomposition, there is a marked tendency for oxalacetic acid to build up in the system, especially in the early stages of the reaction, since the spontaneous decomposition rate no longer is fast enough to eliminate the effects of equilibrium on the transamination reaction.

The decomposition of oxalacetic acid may be catalyzed by the presence of inorganic multivalent metal ions, such as $Al^{+3}$, $Al^{+4}$, $Ni^2$, $Mn^{+2}$, $Mg^{+2}$, $Pb^{+2}$, $Ag^{+2}$, $Fe^{+2}$, $Fe^{+3}$, $Zn^{+2}$, $Cr^{+2}$, $Cr^{+3}$, $Co^{+2}$, $Co^{+3}$, $Pd^{+2}$, $Au^{+3}$, etc., or salts thereof. For example, the metal ions may be added in soluble form, such as the sulfate, sulfide or chloride salts of these metals. In the process of the present invention, particles of metals such as alumina, lead, zinc or iron, may be added as the catalyst. Solid pieces of metal will be advantageous from the process view-point since the catalyst will not be lost with the product stream. The size and shape of the metal pieces is not critical and will depend on the system in which the transamination is conducted. It would also be effective to conduct the reaction in a vessel lined or partially lined with the desired metal compound.

The solid metal particles added to catalyze oxalacetic acid decomposition according to this invention will be alumina (aluminum oxide), ferric oxide, lead oxide or zinc oxide. These metal compounds are considered to be insoluble in water, as taught, for example, in Lange's Handbook of Chemistry, Table 4-1 "Physical Constants of Inorganic Compounds", (12th Ed., 1979). The following chart lists the solubilities of these compounds in water (from Handbook of Chemistry and Physics, "Physical Constants of Inorganic Compounds" (56th Ed., 1975-76), which can be expected to approximate their solubilities in the aqueous systems of this invention:

| Compound | Solubility |
| --- | --- |
| Aluminum oxide | $2.0 \times 10^{-5}$ moles $Al^{+3}$/L |
| Ferric oxide | $1.7 \times 10^{-5}$ moles $Fe^{+2}$/L |
| Lead oxide | $7.6 \times 10^{-5}$ moles $Pb^{+2}$/L |
| Zinc oxide | $1.9 \times 10^{-5}$ moles $Zn^{+2}$/L |

Referring to this chart, it can be appreciated that only very minor amounts of free multivalent metal ion will be present in the transamination system by virtue of the addition of these solid metals. Nonetheless, the solid metals quite satisfactorily catalyze the decomposition of oxalacetic acid in the transamination described herein. In fact, the results of Example V demonstrate that the addition of alumina pellets out-performed the addition of aluminum salts even though the aluminum ions were present at a much higher concentration with the addition of the salts.

The ability of these solid metals to catalyze the decomposition of oxalacetic acid in a transamination reaction system is at once surprising and beneficial. It has been found that for the use of soluble metal salts, the presence of at least about $1.0 \times 10^{-4}$ moles of the ion per liter begins to cause a detectable catalysis of oxalacetic acid decomposition. At metal ion concentrations above about $1.0 \times 10^{-1}$ moles per liter there will be little or no significant increase in the decomposition rate. The preferred range when using metal salts typically will be about $1.0 \times 10^{-3}$ to about $1.0 \times 10^{-1}$ moles of metal ion per liter. By sharp contrast, the addition of solid metal particles to the system adds metal ions only on the order of $10^{-5}$ moles per liter, which is one or more orders of magnitude less than the concentration required with the addition of soluble metal salts. In addition to the much lower initial loading of the metal ion catalyst, the catalyst is conserved when used in solid form, since the particles are retained in the reactor rather than being lost with the product.

The multivalent metal ions useful for catalyzing the decomposition of oxalacetic acid also are responsible for some decomposition of the $\alpha$-keto acid precursor. However, the rate of catalyzed oxalacetic acid decomposition is sufficiently high that the relative quantities of precursor decomposed are unimportant in the overall reaction. That is, the transamination proceeds at a pace which allows relatively little precursor to decompose.

The metal ions will increase the decomposition reaction rate by at least two orders of magnitude over the spontaneous rate of about $6.7 \times 10^{-3}$ moles per liter per hour, even at very low concentrations. For example, at high oxalacetic acid concentrations, about 0.1 moles per liter, the catalyzed decomposition rate may be about 0.1 to 2.0 moles per liter per hour. At lower oxalacetic acid concentrations, about 0.02 moles per liter, the catalyzed decomposition rate may be about 0.01 to 0.2 moles per liter per hour. This rate variation is due to variations in the effectiveness and concentration of the metal catalyst used, as well as the temperature and pH of the reaction. In these ranges, the inhibition of the transamination rate by the presence of oxalacetic acid in the system is effectively eliminated. In the presence of these multivalent metal ions, volumetric transamination rates up to about 10.0 moles per liter per hour in the early stages of conversion and about 0.05 to 0.2 moles per liter per hour overall may be achieved with no indication of oxalacetic acid inhibition.

The cell or enzyme preparation is contacted by the aspartic acid-precursor solution in a suitable reaction vessel in the presence of solid metal particles as described above. The reaction conditions for the process of this invention should be selected to enhance enzyme stability and will be determined according to the overall transamination reaction system selected. The temperature range may be about 20° to about 50° C., preferably about 30° to about 40° C. The pH may be about 6.5 to about 10.0, preferably about 7.5 to about 8.5. The pH adjustment may be made with any base compatible with the enzyme system, preferably with ammonia or potassium hydroxide, either of which will help solubilize the amino acid precursor and aspartic acid. The reaction does not require aeration, unless live, growing cells are used, but there should be some agitation or movement of the cells relative to the substrate in order to maximize biocatalyst-substrate interaction.

The transamination reaction can be expected to be completed in less than about 40 hours, preferably less than 4 hours when high biocatalyst concentrations are employed. Another indicator will be the specific rate of reaction, that is, moles of amino acid produced per gram dry cell weight per hour. In the process of this invention this indicator may range from about 0.0001 to about 0.1, preferably about 0.002 to about 0.05 moles amino acid produced per gram dry cell weight per hour. Typically, however, the specific rate will be about 0.0005 to about 0.01 moles amino acid per gram dry cell weight per hour.

The decomposition products of oxalacetic acid are carbon dioxide and pyruvic acid. The carbon dioxide will dissipate if the reaction is conducted in an open vessel and the pH is close to neutral or it may be collected either for disposal or for use in other processes. If the pH is above about 7.5, the carbon dioxide will remain dissolved in the solution. At least a minute portion of the pyruvic acid is believed to be converted to alanine by transamination or by decarboxylation with aspartic acid. The relative amount of alanine formed will vary with the biocatalyst used in the transamination. Thus, both pyruvic acid and small amounts of alanine will be present, but both may be easily removed by conventional separation methods.

The improved biological transamination of this invention can result in extremely high amino acid yields relative to both aspartic acid and the amino acid precursor. That is, 90% or more of the aspartic acid may be transaminated in the reaction and 90% or more of the precursor may be converted to amino acid. Moreover, the transamination rate is greatly increased, which leads to both increased yields and decreased reaction times. After the reaction is complete, the amino acid product may be recovered by conventional methods. Typical methods of recovery of the desired product may include ion exchange and/or fractional crystallization processes.

The examples which follow are given for illustrative purposes and are not meant to limit the invention described herein. The examples which demonstrate the use of soluble metal salts are intended for comparative purposes. The following abbreviations have been used throughout in describing the invention:

Ag - silver
Al - aluminum
Au - gold
°C. - degrees Centigrade
Co - cobalt
Cr - chromium
Cu - copper
DS - Developing Solution
Fe - iron
g or gm - grams(s)
L or l - liter
M - molar
Mg - magnesium
$\mu$ - micro
ml - milliliter(s)
Mn - manganee
Na - sodium
Ni - nickel
OD - optical density
P-5-P - pyridoxal-5-phosphate
Pb - lead
Pd - palladium
% - percent
PPA - phenylpyruvic acid
ppm - parts per million
TYR - tyrosine
Zn - zinc In the Tables which illustrate the results obtained in the Examples, Specific Rate, Volumetric Rate and Yield are calculated as follows:

$$\text{Specific Rate} = \frac{\text{moles produced}}{\text{grams cells-hour}}$$

$$\text{Volumetric Rate} = \frac{\text{moles produced}}{\text{liter-hour}}$$

$$\text{Yield} = \frac{\text{moles produced}}{\text{moles theoretical limit}}$$

The theoretical limit is based on the moles of precursor or aspartic acid available.

EXAMPLE I (Effect of Manganese Ions on Transaminase Activity)

A synthetic solution was prepared comprising 17.4 gm/l sodium phenylpyruvic acid (Na-PPA) (monohydrate) (Sigma Chemical Co.) and 11.09 gm/l aspartic acid (Sigma Chemical Co.) in a 0.1 M phosphate buffer with 0.1 $\mu$M pyridoxal-5-phosphate (P-5-P), pH adjusted to 7.5 with aqueous ammonia and sulfuric acid. Six 100 ml samples were prepared. To three samples, $1.0 \times 10^{-3}$ M $MnSO_4$ was added; the remaining samples were used as controls. The solutions were added to 150 ml jacketed stir cups, which were held at 37° C. and maintained under mild agitation.

A dried cell preparation was made in the following manner: *Pseudomonas pseudoalcaligenes* ATCC 12815 was grown in 14 liters Trypticase Soy Broth for 24 hours at 35° C. The cells were harvested by centrifugation and dried in a vacuum oven at 37° C. for 12 hours.

Dried cells were added in amounts of 10, 5 and 2 grams per liter to the experimental and control solutions. The solutions were maintained at about 37° C. with mild agitation. Samples were taken at 5 and 24 hours for analysis, by ferric chloride colorimetric assay for PPA (procedures described below) and by HPLC for phenylalanine and aspartic acid. The results are shown in Table I. It is apparent that for the control samples, i.e., without the addition of the metal salt, the volumetric transamination rate remains constant despite heavier catalyst loading. The addition of $MnSO_4$ led to a dramatic increase in the volumetric and specific transamination rates as compared with the control, in addition to higher yields of L-phenylalanine.

TABLE I

| | (Addition of $Mn^{+2}$) | | | | | |
|---|---|---|---|---|---|---|
| Time: | 5 Hours | | | 24 Hours | | |
| Catalyst loading: | 10 g/l | 5 g/l | 2 g/l | 10 g/l | 5 g/l | 2 g/l |
| Control (no $Mn^{+2}$) | | | | | | |
| PPA (g/l) | 4.70 | 3.80 | 4.60 | 0.70 | 0.80 | 0.50 |
| ASP (g/l) | 3.77 | 2.20 | 2.93 | 2.28 | 4.50[1] | 1.60 |
| PHE (g/l) | 8.61 | 8.20 | 7.68 | 11.55 | 10.55 | 10.20 |
| ALA (g/l) | — | — | — | — | — | — |
| Specific Rate | .00104 | .002 | .0046 | .0003 | .0005 | .0012 |
| Volumetric Rate | .0104 | .01 | .01 | .003 | .0027 | .0025 |
| Yield (PHE/PPA) | 62% | 62% | 57% | 84% | 76% | 75% |
| Yield (PHE/ASP) | 62% | 62% | 57% | 95% | 120% | 89% |
| Experimental ($1.0 \times 10^{-3}$ M $Mn^{+2}$ added) | | | | | | |
| PPA (g/l) | 0.30 | 1.25 | 3.89 | 0.05 | 0.40 | 0.30 |
| ASP (g/l) | 2.84 | 2.77 | 5.08 | 0.69 | 1.00 | 1.34 |
| PHE (g/l) | 12.69 | 10.67 | 7.67 | 13.95 | 12.47 | 12.16 |
| ALA (g/l) | 0.62 | 0.27 | — | 0.84 | 0.79 | 0.43 |
| Specific Rate | .0015 | .0026 | .0046 | .00035 | .0006 | .0015 |
| Volumetric Rate | .015 | .013 | .01 | .0035 | .0031 | .003 |
| Yield (PHE/PPA) | 93% | 78% | 57% | 101% | 90% | 88% |
| Yield (PHE/ASP) | 93% | 78% | 57% | 106% | 99.6% | 101% |

[1] Apparent analytical error.

EXAMPLE II (Effect of Magnesium Ions on Transaminase Activity)

A synthetic solution was prepared comprising 7.71 gm/l Na-PPA (monohydrate) (Sigma Chemical Co.) and 12.35 gm/l aspartic acid (Sigma Chemical Co.) in 0.05 M phosphate buffer with $1.0 \times 10^{-2}$ M $MgSO_4$ and 0.1 μM P-5-P, pH adjusted to 7.5 with aqueous ammonia and sulfuric acid. Aliquots of 100 ml were placed in five 150 ml jacketed stir cups, heated to 37° C. and maintained under mild agitation. Dried *Pseudomonas pseudoalcaligenes* ATCC 12815 cells were prepared as in Example I. The cells were added to the cups in the following amounts: 15, 10, 5.0, 2.0 and 1.0 grams per liter, respectively. Samples were taken at 1 and 24 hours and analyzed as in Example I. The results, shown in Table II, indicate that with the addition of $MgSO_4$ no oxalacetic acid repression of the transamination is observed, and the volumetric reaction rates as well as overall yields were increased.

TABLE II

| | (Addition of $Mg^{+2}$) | | | | | | | |
|---|---|---|---|---|---|---|---|---|
| Time: | 1 Hour | | | | 24 Hours | | | |
| Catalyst loading: | 15 g/l | 10 g/l | 5 g/l | 1 g/l | 15 g/l | 10 g/l | 5 g/l | 1 g/l |
| PPA (g/l)* | 8.81 | 9.76 | 11.00 | 13.84 | 0.00 | 0.15 | 0.15 | 0.95 |
| ASP (g/l) | 9.44 | 10.29 | 10.13 | 11.75 | 0.92 | 0.93 | 1.18 | 2.08 |
| PHE (g/l) | 7.96 | 4.60 | 2.99 | 0.57 | 14.18 | 13.87 | 13.52 | 11.47 |
| ALA (g/l) | — | — | — | — | 0.52 | 0.35 | 0.19 | 0.79 |
| Specific Rate | .0032 | .0028 | .0036 | .0035 | .00024 | .00035 | .00068 | .0029 |
| Volumetric Rate | .048 | .028 | .018 | .0035 | .0036 | .0035 | .0034 | .0029 |
| Yield (PHE/PPA) | 56% | 32% | 21% | 4% | 100% | 98% | 96% | 81% |

*as phenylpyruvic acid

EXAMPLE III (Effect of Magnesium Ion Concentration on Transaminase Activity)

A synthetic solution was prepared comprising 17.0 gm/l Na-PPA (monohydrate) (Sigma Chemical Co.) (sodium salt) and 11.0 gm/l aspartic acid (Sigma Chemical Co.) in a 0.1 M phosphate buffer with $1.0 \times 10^{-4}$ M P-5-P, pH adjusted to 7.5 with aqueous ammonia and sulfuric acid. Aliquots of 100 ml were placed in jacketed stir cups with varying amounts of magnesium sulfate to achieve the $Mg^{+2}$ concentrations indicated in Table III. The solutions were held at 37° C. and maintained under mild agitation. Dried *Pseudomonas pseudoalcaligenes* ATCC 12815 cells were prepared as in Example I. To each solution, 0.5 gm of dried cells were added. Samples were analyzed as in Example I at 0, 2 and 5 hours. The results, shown in Table III, indicate that increasing concentrations of $Mg^{+2}$ ions correspond to increasing transamination rates and overall yields.

TABLE III

| | (Varying Concentrations of $Mg^{+2}$) | | | | | |
|---|---|---|---|---|---|---|
| $Mg^{+2}$ concentration: (moles/liter) | 0 | $3 \times 10^{-4}$ | $1 \times 10^{-3}$ | $3 \times 10^{-3}$ | $1 \times 10^{-2}$ | $3 \times 10^{-2}$ |
| 0 Hours | | | | | | |
| PPA (g/l)* | 17.20 | 17.00 | 16.70 | 16.90 | 17.20 | 17.10 |
| ASP (g/l) | 13.00 | 13.30 | 13.20 | 13.40 | 13.30 | 13.90 |
| 2 Hours | | | | | | |
| PPA (g/l)* | 9.96 | 7.82 | 7.03 | 6.40 | 8.02 | 9.01 |
| ASP (g/l) | 5.92 | 3.00 | 2.50 | 3.30 | 3.44 | 3.45 |
| PHE (g/l) | 8.93 | 11.73 | 12.80 | 11.52 | 11.07 | 11.60 |
| Specific Rate | .0054 | .007 | .0078 | .007 | .0067 | .007 |
| Volumetric Rate | .027 | .036 | .039 | .035 | .034 | .035 |
| 5 Hours | | | | | | |
| PPA (g/l)* | 6.50 | 2.40 | 2.21 | 2.63 | 2.12 | 2.70 |

TABLE III-continued (Varying Concentrations of $Mg^{+2}$)

| $Mg^{+2}$ concentration: (moles/liter) | 0 | $3 \times 10^{-4}$ | $1 \times 10^{-3}$ | $3 \times 10^{-3}$ | $1 \times 10^{-2}$ | $3 \times 10^{-2}$ |
|---|---|---|---|---|---|---|
| ASP (g/l) | 2.70 | 1.00 | 1.00 | 1.00 | 1.00 | 1.00 |
| PHE (g/l) | 12.70 | 15.20 | 15.40 | 15.60 | 16.00 | 15.90 |
| Specific Rate | .003 | .0037 | .0037 | .0038 | .0039 | .0039 |
| Yield (PHE/PPA) | 74.0% | 80.4% | 92.0% | 92.0% | 93.0% | 93.0% |

*as phenylpyruvic acid

EXAMPLE IV (Effect of Various Salts on Transaminase Activity)

A synthetic solution was prepared comprising 0.6 gm/l Na-PPA (monohydrate) (Sigma Chemical Co.) and 13.5 gm/l aspartic acid (Sigma Chemical Co.) in a 0.1 M phosphate buffer with 0.1 µM P-5-P. Samples of 100 ml of this solution were prepared and $1.0 \times 10^{-3}$ moles per liter of one of the following salts was added to each sample: magnesium sulfate, manganese sulfate, copper sulfate, calcium chloride, aluminum sulfate and iron sulfate. One sample was maintained as a control, with no salts added. Each solution was pH adjusted to 8.5 and mildly agitated. Dried *Pseudomonas pseudoalcaligenes* ATCC 12815 cells were prepared as in Example I. To each solution, 0.5 gm of dried cells were added. The solutions were maintained at 37° C. under mild agitation. Samples were taken at 0, 5 and 24 hours and analyzed as in Example I. The results, shown in Table IV, indicate that the $Mg^{+2}$, $Mn^{+2}$, $Al^{+3}$ and $Fe^{+2}$ salts are effective in increasing transamination rate and yield.

EXAMPLE V (Comparison of Soluble and Insoluble Metals)

A synthetic solution was prepared comprising 30.0 gm/l Na-PPA (monohydrate) (Sigma Chemical Co.) and 24.0 gm/l aspartic acid (Sigma Chemical Co.) in 0.1 M phosphate buffer with 0.1 µM P-5-P and 100 ppm Barquat MB-SO (TM) (Lonza Inc.) as a disinfectant. One of the following was added to respective 100 ml aliquots of the solution: $1.0 \times 10^{-3}$ M $MgSO_4$, $1.0 \times 10^{-m}$ $MgSO_4$, $1.0 \times 10^{-2}$ M $Al_2(SO_4)_3$, and 10 gm/l alumina pellets (approximately 40 mesh). The solutions were pH adjusted to 8.5 with aqueous ammonia and sulfuric acid. To each solution was added 5.0 gm wet *Pseudomonas pseudoalcaligenes* ATCC 12815 cells (72% moisture). The solutions were heated to 35° C. and maintained under mild agitation. Samples were taken at 0, 1, 5 and 24 hours and analyzed as in Example I. The results, shown in Table V, indicate that the use of alumina pellets is approximately as effective as magnesium sulfate or aluminum sulfate for increasing the volumetric reaction rate and overall yield for the transamination.

TABLE IV (Comparison of Various Salts)

| | $MgSO_4$ | $MnSO_4$ | $CuSO_4$ | $CaCl_2$ | $Al_2(SO_4)_3$ | $FeSO_4$ | Control |
|---|---|---|---|---|---|---|---|
| 0 Hours | | | | | | | |
| PPA (g/l)* | 16.30 | 16.04 | 16.30 | 16.20 | 16.55 | 15.90 | 16.40 |
| ASP (g/l) | 13.10 | 15.50 | 13.74 | 14.40 | 12.74 | 14.34 | 14.32 |
| 5 Hours | | | | | | | |
| PPA (g/l)* | 8.33 | 6.33 | 9.00 | 8.10 | 8.30 | 9.30 | 6.20 |
| ASP (g/l) | 4.47 | 5.47 | 9.00 | 16.80 | 4.90 | 6.93 | 8.20 |
| PHE (g/l) | 8.44 | 8.59 | 3.09 | 2.75 | 8.85 | 7.10 | 6.20 |
| Volumetric Rate | .011 | .011 | .0037 | .0033 | .011 | .009 | .007 |
| Specific Rate | .002 | .0021 | .00075 | .00067 | .0021 | .0018 | .0017 |
| 24 Hours | | | | | | | |
| PPA (g/l)* | 0.00 | 0.00 | 2.20 | 1.70 | 0.00 | 0.00 | 0.00 |
| ASP (g/l) | 0.97 | 1.27 | 8.90 | 5.74 | 1.68 | 3.20 | 4.10 |
| PHE (g/l) | 15.50 | 14.90 | 6.86 | 4.95 | 14.95 | 14.00 | 13.20 |
| Yield (PHE/PPA) | 94.9% | 93.0% | 45.0% | 30.0% | 90.0% | 88.0% | 80.0% |
| Yield (PHE/ASP) | 95.0% | 78.0% | 60.0% | 36.0% | 95.0% | 80.0% | 74.0% |

*as phenylpyruvic acid

TABLE V (Alumina pellets vs. metal salts)

| | Metal Catalyst: | | | |
|---|---|---|---|---|
| | $1 \times 10^{-3}$ M $MgSO_4$ | $1 \times 10^{-2}$ M $MgSO_4$ | $1 \times 10^{-2}$ M $Al_2(SO_4)_3$ | 10 g/l Alumina Pellets |
| 0 Hours | | | | |
| PPA (g/l)* | 23.54 | 23.07 | 23.82 | 23.83 |
| ASP (g/l) | 23.20 | 24.07 | 24.00 | 24.03 |
| 1 Hour | | | | |
| PPA (g/l)* | 16.52 | 15.31 | 17.40 | 15.17 |
| ASP (g/l) | 18.49 | 17.73 | 20.20 | 16.04 |
| PHE (g/l) | 7.18 | 9.18 | 6.40 | 8.59 |
| Volumetric Rate | .044 | .053 | .038 | .052 |
| Specific Rate | .0031 | .0038 | .0028 | .0037 |
| 5 Hours | | | | |

TABLE V-continued (Alumina pellets vs. metal salts)

| | Metal Catalyst: | | | |
|---|---|---|---|---|
| | $1 \times 10^{-3}$ M MgSO$_4$ | $1 \times 10^{-2}$ M MgSO$_4$ | $1 \times 10^{-2}$ M Al$_2$(SO$_4$)$_3$ | 10 g/l Alumina Pellets |
| PPA (g/l)* | 2.84 | 2.10 | 4.57 | 2.07 |
| ASP (g/l) | 7.73 | 6.22 | 7.73 | 6.02 |
| PHE (g/l) | 19.05 | 19.74 | 19.05 | 21.95 |
| Volumetric Rate | .025 | .024 | .023 | .027 |
| Specific Rate | .0016 | .0017 | .0016 | .0019 |
| 24 Hours | | | | |
| PPA (g/l)* | 0.00 | 0.00 | 0.00 | 0.00 |
| ASP (g/l) | 4.69 | 3.47 | 4.80 | 3.46 |
| PHE (g/l) | 23.45 | 22.79 | 22.20 | 22.75 |
| Yield (PHE/PPA) | 99.6% | 98.9% | 93.0% | 95.5% |

*as phenylpyruvic acid

EXAMPLE VI (Production of Tyrosine)

A synthetic solution was prepared by dissolving 1.25 gm p-hydroxy phenylpyruvic acid (pH-PPA) (Sigma Chemicl Co.) in 50 ml 0.1 M phosphate buffer along with 1.0 gm aspartic acid (Sigma Chemical Co.), 0.1 µM-P-5-P, and $1.0 \times 10^{-3}$ M/l zinc sulfate. The pH of the solution was adjusted to 8.0. *E. coli* ATCC 11303 cells were immobilized in Hypol (TM)(HFP 3000, W. R. Grace & Co.) polyurethane foam prepared by mixing 50.0 gm of a 75% moisture cell paste with 50.0 gm of the Hypol (TM) prepolymer. The mixture was allowed to cure (about 15 minutes) and the cured foam was cut into small pieces approximately ¼ inch in size. A total of 4.0 gm cured foam was added to the prepared pH-PPA solution. The solution was maintained at 37° C. with mild agitation.

Samples were taken at 0, 3 and 18 hours and analyzed by thin layer chromatography (TLC) and HPLC for tyrosine and aspartic acid. After 3 hours, the solution became hazy with precipitate as tyrosine was produced. To recover the product, the slurry and foam were washed with an equal volume of acetone and the foam filtered out with a Buchner funnel. The solution, which comprised about 1.2 gm/l tyrosine in solution, was centrifuged at 3000 RPM. The resulting pellet of amino acid was collected and dried. A total of 1.1 gm dried product was collected and identified by TLC and HPLC as tyrosine. The product was found to have a purity of >90% by non-aqueous titration. The results, shown in Table VI, indicate that the method described herein is suitable for the rapid production of tyrosine in high yields.

TABLE VI (Production of Tyrosine)

| | Time: | | |
|---|---|---|---|
| | 0 Hours | 3 Hours | 18 Hours |
| pH-PPA (g/l) | 25.0 | — | — |
| ASP (g/l) | 18.5 | 16.2 | 1.2 |
| TYR[1] | 0.0 | 1.2 | 1.2 |
| TYR[2] | 0.0 | — | 1.0 |
| Yield (TYR/pH-PPA) | — | — | 85% |
| Yield (TYR/ASP) | — | — | 80% |

[1] Gm/l tyrosine in solution at time of sample
[2] Gm tyrosine as total yield in dried pellet Ferric Chloride Colorimetric Assay For Phenylpyruvic Acid, Sodium Salt Principle: Phenylpyruvic acid (PPA) forms a green complex with ferric ions. The intensity of the green color is proportional to the amount of PPA present.

Reagents:

1 Developing Solution (DS) (1000 ml) - Mix the following ingredients and cool to room temperature in an ice bath. Add contents to a one liter volumetric flask and bring up to volume with deionized water. Ingredients: 0.5 gm FeCl$_3$.6H$_2$O; 20 ml glacial acetic acid; 600 ml dimethyl sulfoxide; 200 ml deionized water.

2. Na-PPA Standard Solution (10 gm/l) - Add 500 mg Na-PPA H$_2$O (Aldrich Chemical Co., Inc., 98% - 100% pure) to 40 ml 0.1 M Tris/HCl buffer (pH 8.0) at 34° C. Stir until dissolved. Place solution in a 50 ml volumetric flask and bring up to volume with Tris/HCl buffer. Store refrigerated. For 0.1 M Tris/HCl buffer: add 900 ml deionized water to 12.11 gm Tris; adjust pH to 8.0 with HCl; pour into volumetric flask; add deionized water to 1000 ml.

Calibration Curve:

Add Na-PPA Standard Solution and 4.95 ml of Developing Solution to glass spectrophotometer tubes. Mix on vortex. Allow to stand for exactly 10 minutes (start timing with the addition of DS to first tube). Read optical density (OD) at 640 nm. Prepare Na-PPA.H$_2$O Standard Calibration curve (vertical axis is absorbance; horizontal axis is mg Na-PPA.H$_2$O/ml DS).

| NA-PPA Standard | mg Na-PPA H$_2$O per ml DS |
|---|---|
| 5 µl | 0.01 |
| 10 µl | 0.02 |
| 15 µl | 0.03 |
| 20 µl | 0.04 |
| 25 µl | 0.05 |
| 30 µl | 0.06 |

Calculation:

$$\text{Na—PPA H}_2\text{O (mg/ml)} = \frac{\text{OD} \times 100 \times \text{dilution}}{\text{slope from standard curve}}$$

or $$\text{PPA (gm/l)} = \frac{\text{OD} \times 100 \times \text{dilution}}{\text{slope from standard curve}} \times \frac{164.4}{204.16}$$

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. An improved process for providing metal ions to a transamination process in order to drive the transamination of an amino acid precursor to its corresponding L-amino acid by catalyzing decomposition of the oxalacetic acid transamination by-product, said transamination process comprising
    (a) selecting aspartic acid as the amino donor,
    (b) selecting the appropriate α-keto acid as the amino acid precursor,
    (c) selecting a suitable intra- or extracellular transaminase,
    (d) coupling the transamination reaction with the catalyzed decomposition of the oxalacetic acid transamination by-product, under conditions favorable for transaminase activity, said catalyzed decomposition effected by adding to the reaction system multivalent metal ions, and
    (e) allowing the transamination to proceed,
the improvement comprising adding said multivalent metal ions to said transamination reaction system by providing solid particles or pieces comprising aluminum oxide, ferric oxide, lead oxide or zinc oxide to said system.

2. The process of claim 1 in which said metal pieces are in the form of a metal lining or partial metal lining of the reaction vessel.

3. The process of claim 1 in which said α-keto acid precursor and said L-amino acid are selected from the group comprising the following pairs: phenylpyruvic acid to produce L-phenylalanine, α-ketoisocaproic acid to produce L-leucine, α-ketoisovaleric acid to produce L-valine, pyruvic acid to produce L-alanine, β-hydroxy-α-ketobutyric acid to produce L-threonine, p-hydroxyphenylpyruvic acid to produce L-tyrosine, indole pyruvic acid to produce L-tryptophan, α-ketohistidinal acid to produce L-histidine and α-keto-β-methylvaleric acid to produce L-isoleucine.

4. The process of claim 3 in which L-amino acid is L-phenylalanine.

* * * * *

UNITED STATES PATENT AND TRADEMARK OFFICE
CERTIFICATE OF CORRECTION

PATENT NO. : 4,859,591
DATED : August 22, 1989
INVENTOR(S) : James F. Walter and Martin B. Sherwin It is certified that error appears in the above-identified patent and that said Letters Patent is hereby corrected as shown below:

In the specification:

Column 4, line 39, "20 indole" should read --indole--.

Column 4, line 66, "amno" should read --amino--.

Column 11, lines 15-16 (Example IV):

"0.6 gm/l" should read --20.6 gm/l--.

Column 12, line 22 (Example V):

"$1.0 \times 10^- M\ MgSO_4$," should read --$1.0 \times 10^{-2}\ M\ MgSO_4$,--.

Signed and Sealed this

Third Day of July, 1990

Attest:

HARRY F. MANBECK, JR.

Attesting Officer

Commissioner of Patents and Trademarks